United States Patent [19]

McDermed et al.

[11] Patent Number: 5,102,914

[45] Date of Patent: Apr. 7, 1992

[54] ANTIHYPERTENSIVE SULFONANILIDES

[75] Inventors: John D. McDermed, Chapel Hill; Anjaneyulu S. Tadepalli, Durham, both of N.C.; Vincent H. Chang, Freeport, The Bahamas; Kevin P. Hurley, Durham, N.C.

[73] Assignee: Burroughs Wellcome Co., Research Triangle Park, N.C.

[21] Appl. No.: 455,909

[22] Filed: Dec. 18, 1989

Related U.S. Application Data

[63] Continuation of Ser. No. 340,226, Apr. 19, 1989, abandoned.

[30] Foreign Application Priority Data

Apr. 20, 1988 [GB] United Kingdom ............... 8809314

[51] Int. Cl.⁵ .................... A61K 31/18; C07C 143/74
[52] U.S. Cl. ...................................... 514/605; 564/99
[58] Field of Search ........................ 564/99; 514/605

[56] References Cited

U.S. PATENT DOCUMENTS 4,044,150  8/1977  Kreighbaum et al. ............... 564/99

FOREIGN PATENT DOCUMENTS 1962497  6/1971  Fed. Rep. of Germany .

OTHER PUBLICATIONS

Schliker, et al., Journal of Cardiovascular Pharmacology, 6:1238–1244, 1984, Increased Afinity and Preference of Halogenated Derivatives of BE 2254 for α1-Adrenoceptors Demonstrated by Functional and Binding Experiments.

Repke, et al., Journal of Pharmaceutical Sciences, vol. 74, No. 1, Jan. 1985, Syntheses and Hypotensive Properties of Substituted 2-Aminotetralins.

Drug Evaluation, Drugs 34: 311–349, (1987), Singh, et al., Sotalol-A Review of its Pharmacodynamic and Pharmacokinetic Properties, and Therapeutic Use.

J. Org. Chem. 1985, 50, 5446–5448—Diisopincampheylchloroborane, A Remarkably Efficient Chiral Reducing Agent for Aromatic Prochiral Ketones.

Aldrichimica Acta, vol. 20, No. 1, 1987—I. Chiral Reducing Agents.

JAMA, Dec. 11, 1967, vol. 202, No. 11, pp. 116–112, Effects of Treatment on Morbidity in Hypertension, Results in Patients with Diastolic Blood Pressure Averaging 115 through 129 mm Hg.

JAMA, Aug. 17, 1970, vol. 213, No. 7, pp. 1143–1152, Effects of Treatment on Morbidity in Hypertension, II. Results in Patients with Diastolic Blood Pressure Averaging 90 through 114 mm Hg.

Current Therapy, 1981, Hypertension, pp. 219–223.

Temple, et al., Journal of Medicinal Chemistry, 1976, vol. 19, No. 5, pp. 626–633, Adrenergic Sulfonanilides. 4, Centrally Active β-Adrenergic Agonists.

Primary Examiner—Richard L. Raymond
Assistant Examiner—B. Bembenick
Attorney, Agent, or Firm—Donald Brown; Hannah O. Green; Lawrence A. Nielsen

[57] ABSTRACT

The present invention is concerned with compounds of formula (I)

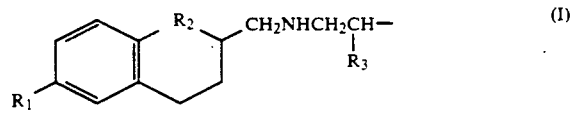

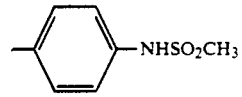

wherein
$R_1$ is hydrogen;
$R_2$ is carbonyl; and
$R_3$ is hydroxy;

and salts thereof, with processes for preparing same and with their use in medicine for the treatment of hypertension.

39 Claims, No Drawings

ANTIHYPERTENSIVE SULFONANILIDES

This is a continuation of copending application Ser. No. 07/340,226 filed on Apr. 19, 1989 (now abandoned).

FIELD OF INVENTION

This invention relates to compounds useful in medicine for the treatment of hypertension, to the synthesis of the compounds, to pharmaceutical formulations containing the compounds and the use of the compounds in medical practice.

These compounds of the instant invention may be characterized by formula (I)

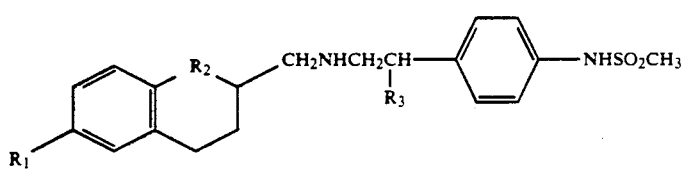

wherein $R_1$ is hydrogen, $R_2$ is C=O, $R_3$ is hydroxy, and pharmaceutically acceptable salts thereof. The invention also includes all enantiomeric and diastereomeric forms of the compounds of formula (I), either individually or admixed in any proportions.

BACKGROUND INFORMATION

Hypertension may be defined as a condition of sustained elevated arterial blood pressure, i.e., a diastolic pressure in excess of 90 mmHg. In the majority of cases, the patients are affected by essential hypertension, which by definition means that the underlying etiologic mechanism(s) is unknown. Regardless of the mechanism, a sustained elevation of blood pressure for a period of time has been shown to result in significant cardiovascular damage throughout the body, e.g., congestive heart failure, coronary artery disease, stroke and progressive renal failure [Veterans Administration Cooperative Study Group on Antihypertensive Agents: Effects of Treatment on Morbidity in Hypertension. Results in patients with diastolic blood pressures averaging 115 through 129 mm Hg, J.A.M.A., (1967), 202, 1028 and Veterans Administration Cooperative Study Group on Antihypertensive Agents: Effects of Treatment on Morbidity in Hypertension II. Results in patients with diastolic blood pressures averaging 90 through 114 mm Hg, J.A.M.A., (1970), 213, 1143].

The benefits of drug therapy to reduce and control blood pressure have been established [Woods, J. W., Current Therapy, ed. Conn, H.F., pp. 219-220, 1981]. Since the specific etiology is not usually known, an empirical approach to the treatment of hypertensive patients is taken. Often, the choice of treatment is based on the severity of the disease and the patient's response and compliance to initial therapy. The goal of the treatment is to reduce elevated blood pressure and maintain pressure at or near normal levels. An antihypertensive agent should be orally active and have a sufficiently prolonged duration of action to normalize hemodynamic derangements in humans.

SUMMARY OF THE INVENTION

The compounds of the present invention, which can be classified as tetralin sulfonanilides, have been found to have antihypertensive properties and are therefore useful in controlling elevated blood pressure in mammals such as humans.

DETAILED DESCRIPTION OF THE INVENTION

Compounds of formula (I) and their salts may be synthesized by methods known in the art for the synthesis of compounds having analogous structures. In particular, compounds of formula (I) and their salts may be prepared by any of the following processes which constitute further aspects of the present invention:

(a) for the preparation of compounds of formula (I) wherein $R_2$ is C=O, reacting a compound of formula (VI)

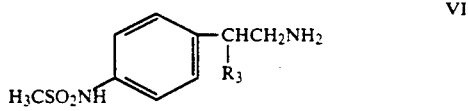

wherein $R_3$ is as hereinbefore defined, with a compound of formula (II)

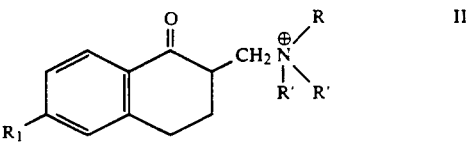

wherein $R_1$ is as hereinbefore defined and R and R' are as hereinbelow defined, or with a compound of formula (IV)

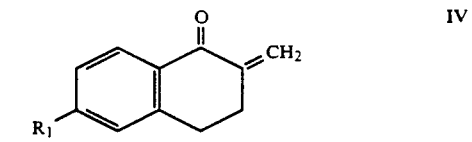

wherein $R_1$ is as hereinbefore defined;

(b) for the preparation of compounds of formula (I) wherein $R_2$ is methylene and $R_3$ is hydroxy, reducing a compound of formula (XIV)

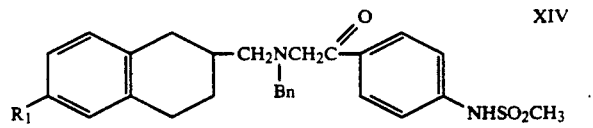

wherein Bn is benzyl and $R_1$ is as hereinbefore defined, by, for example, catalytic hydrogenation using two molecular equivalents of hydrogen over a suitable metal catalyst, such as palladium or platinum, or chemical reduction of the carbonyl group using, for example, a suitable hydride or borane reagent, followed by debenzylation, by, for example, catalytic hydrogenation using one molecular equivalent of hydrogen over a suitable metal catalyst, such as palladium or platinum; or reducing a compound of formula (XVII)

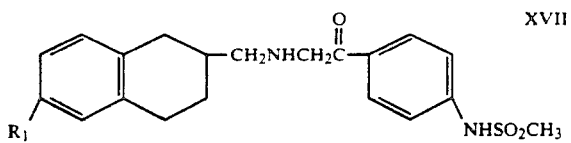

wherein $R_1$ is as hereinbefore defined, using, for example, a suitable hydride or borane reagent.

Thus compounds of formula (I) wherein $R_2$ is C=O are Mannich bases and may be prepared by standard methods well known to chemists. With reference to Scheme 1, one method for preparing such compounds comprises reacting a primary amine of formula (VI) with a quaternary ammonium salt of formula (II) or with a functional equivalent thereof such as the corresponding exo-methylene ketone (IV).

Compounds of formula (II) wherein $R_1$ is hydrogen or methoxy, R is lower alkyl, and R' is lower alkyl or R'R' is an alicyclic ring, may be synthesized by reacting an amine of formula (V) with a suitable alkylating agent RL, where L is a leaving group such as halide, for example, methyl iodide.

The compounds of formula (V) are also Mannich bases and may be synthesized by standard methods, for example, by reacting a ketone of formula (III) with formaldehyde, or a functional equivalent thereof such as paraformaldehyde, and a secondary amine of formula $HN(R')_2$, or a salt thereof, by heating the mixture in a solvent, preferably a lower alcohol, in the presence of acid. Alternatively, primary amines of formula (VI) may be used in lieu of a secondary amine in the Mannich reaction to yield compounds of formula (I) directly. However, those skilled in the art will realize that primary amines give poor yields in such reactions.

Compounds of formula (III), (IV) and (VI) are commercially available or may be prepared by methods available from the chemical literature. Thus compounds of formula (VI), particularly those wherein $R_3$ is hydroxy, may be prepared from numerous possible starting materials via a variety of different routes well documented in the literature and known to chemists. With reference to Scheme 2, one preferred method of preparing compounds of formula (VI) wherein $R_3$ is hydroxy comprises the reduction of compounds of formula (VII) in a single step using three molecular equivalents of hydrogen in the presence of a metal catalyst such as palladium or platinum. The catalyst may be free or deposited on any suitable support such as carbon. Alternatively, compounds of formula (VII) may be reduced to compounds of formula (VI) wherein $R_3$ is hydroxy in two steps. The first step (reduction of the carbonyl group) may be accomplished by reaction with a wide variety of reducing agents well known to those skilled in the art, such as complex hydrides (e.g., $NaBH_4$ or $LiAlH_4$) or borane type reagents (e.g., diborane), to give a compound of formula (VIII) wherein $R_3$ is hydroxy which is then further reduced by catalytic hydrogenation using two molecular equivalents of hydrogen to give the compound of formula (VI).

It will be appreciated by chemists that compounds of formulas (VI) and (VIII) wherein $R_3$ is hydroxy contain an asymmetric carbon atom and that the use of achiral reducing agents in the preparation of these compounds from a compound of formula (VII) will produce racemic products, whereas the use of chiral reducing agents in analogous reactions may produce products enriched in one of the two possible enantiomers. Separately reacting the enantiomers of (VI) with compounds of formula (II) or (IV) in which $R_2$ is carbonyl will produce optically active products composed of two diastereomers. Fractional crystallization of the diastereomers or chromatography of the mixture may result in products which are enriched in one of the possible diastereomers. The methods described for the preparation of compounds of formula (I) in which $R_3$ is hydrogen and $R_2$ is hydroxymethylene result in products containing two chiral carbons which, therefore, can exist as four stereoisomers. Fractional crystallization of the diastereomers or chromatography of the mixture may produce compounds which are enriched in one of the possible diastereomers. Methods described herein for the preparation of compounds of formula (I) in which $R_3$ is hydrogen and $R_2$ is methylene produce compounds with one chiral carbon and which, therefore, exist as enantiomers. Preparation of addition salts from such compounds and a chiral organic acid, followed by fractional crystallization may result in compounds which are enriched in one of the enantiomers; optical resolution of such compounds may also be accomplished by chromatographic methods.

Compounds of formula (VII) may be prepared by reacting dibenzylamine, or a functional equivalent thereof, with a bromoketone, or functional equivalent thereof, of formula (IX).

Compounds of formula (IX) may also be converted to compounds of formula (VI) via the corresponding aminoketone (XI). This conversion may be accomplished by reacting the compound of formula (IX) with ammonia, or a precursor equivalent thereof (e.g., phthalimide or hexamethylenetetramine), followed by reduction of the resulting compound (XI) using one of the methods described above for the initial reduction of compound (VII), to give the compound of formula (VI).

Compounds of formula (VI) may also be obtained by the reduction (e.g., with $LiAlH_4$) of compounds of formula (X).

Compounds of formula (XII) may also be used to synthesize compounds of formula (VI) either directly by reaction with ammonia, or a precursor equivalent thereof (e.g., phthalimide or hexamethylenetetramine), or indirectly by reaction with dibenzylamine, or a functional equivalent thereof, to yield a compound of formula (VIII) which may then be converted to the compound of formula (VI) by the method described above. As indicated earlier, it should be noted that compounds of formula (VIII) wherein $R_3$ is hydroxy contain an asymmetric carbon atom and may be optically active, in which case optically active compounds of formula (VI) will be obtained.

Compounds of formula (IX), (X) and (XII) are commercially available or may be prepared by methods available from the chemical literature.

With reference to Scheme 3, compounds of formula (I) wherein $R_2$ is methylene and $R_3$ is hydroxy may be prepared by the reduction (in one or two steps) of compounds of formula (XIV) by methods similar to those described above for the reduction of compound (VII) to compound (VI).

Compounds of formula (XIV) may be prepared by the alkylation of compounds of formula (XV) with a bromoketone, or functional equivalent thereof, of formula (IX) in a manner analogous to the preparation of compound (VII) described above.

Compounds of formula (I) wherein $R_2$ is methylene and $R_3$ is hydroxy may also be prepared by the reduction of ketones of formula (XVII) by methods well known to those skilled in the art such as that described above for the reduction of compounds of formula (VII) to compounds of formula (VIII).

Compounds of formula (XVII) may be prepared by the alkylation of compounds of formula (XVI) with a bromoketone, or functional equivalent thereof, of formula (IX) in a manner analogous to the preparation of compounds of formula (VII) and (XIV) described above.

Compounds of formula (XV) may be prepared by the N-benzylation of compounds of formula (XVI).

Compounds of formula (IX) and (XVI) are commercially available or may be prepared by methods available from the chemical literature.

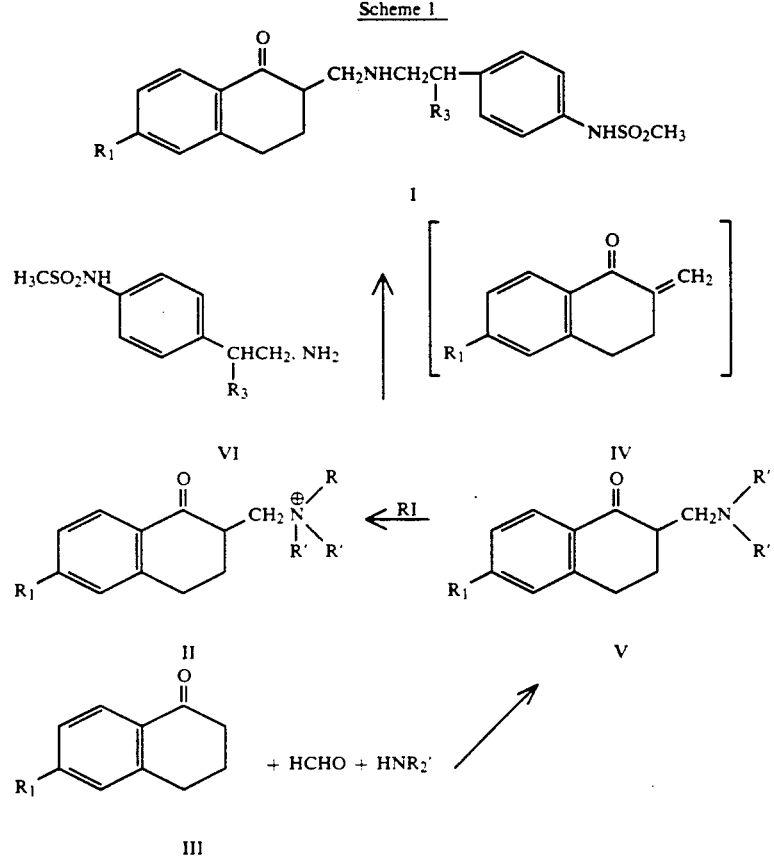

Scheme 1

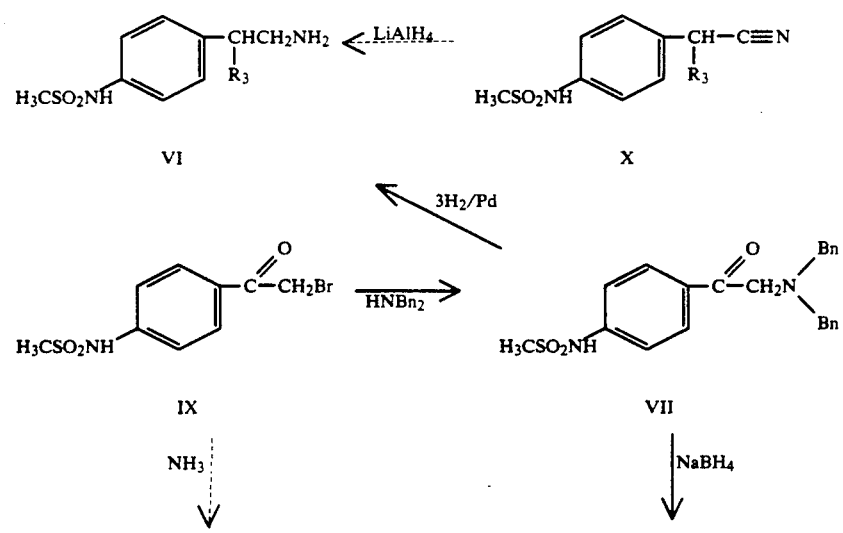

Scheme 2

-continued
Scheme 2
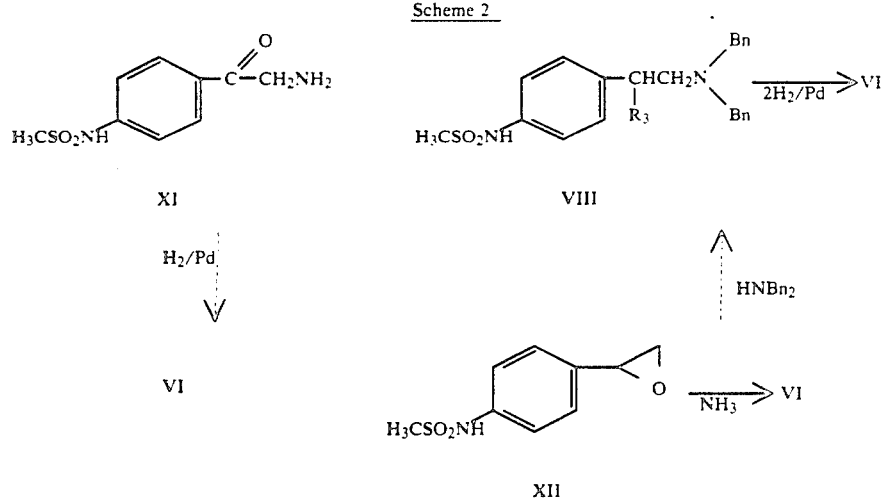
Scheme 3
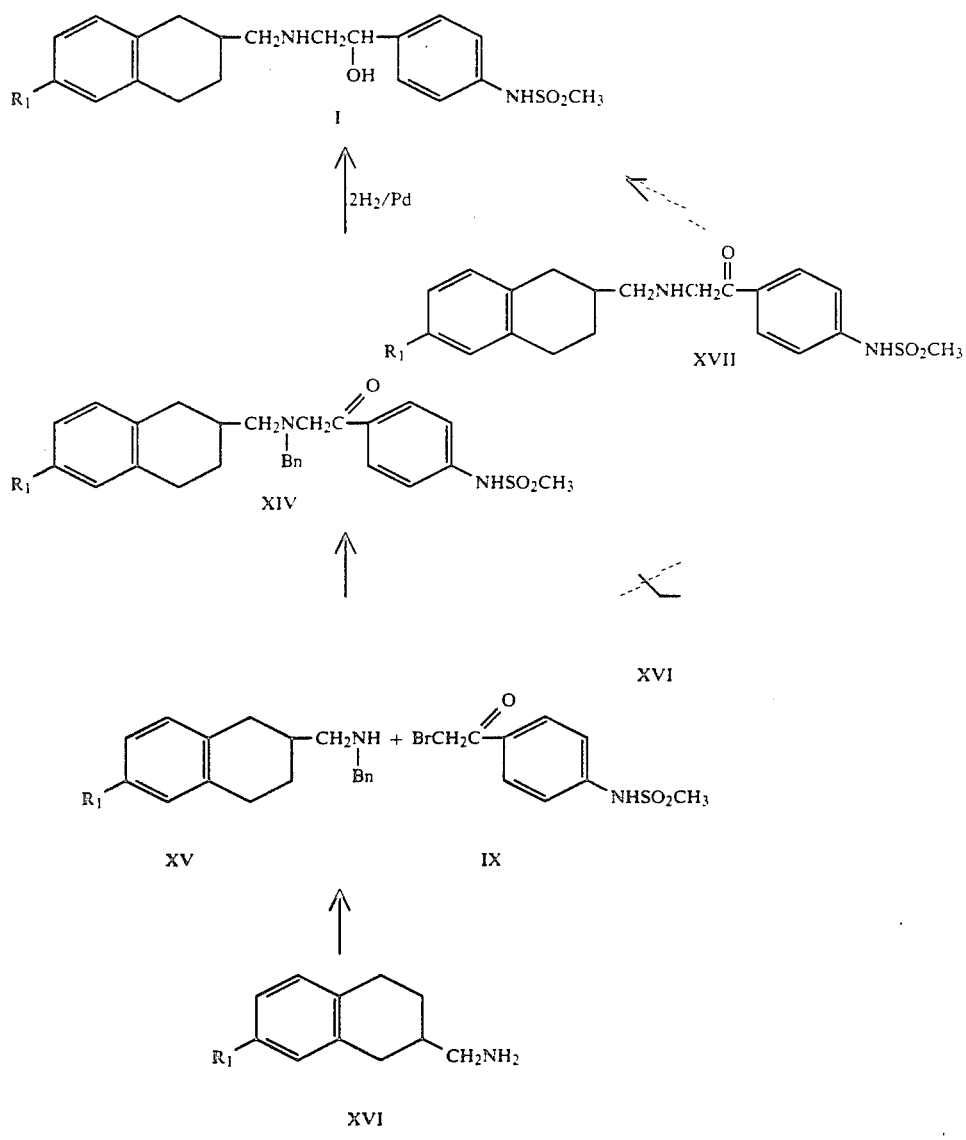

Compounds including those of formula (I) which were found to be active as antihypertensive agents are:

EXAMPLE

| Compound | Example No. | $R_1$ | $R_2$ | $R_3$ | Salt |
|---|---|---|---|---|---|
| XVIIIa,b* | 1 | H | C=O | OH | HCl |
| XIX | 2 | OCH$_3$ | C=O | OH | HCl |
| XX | 3 | OCH$_3$ | C=O | H | HCl |
| XXI | 4 | H | C=O | H | HCl |
| XXII | 5 | H | CH—OH | H | HCl |
| XXIII | 6 | H | methylene | H | HCl |
| XXIV | 7 | H | methylene | OH | HCl |
| XXXVII* | 8 | H | C=O | OH | HCl |
| XXXVIIIa* | 8 | H | C=O | OH | HI |
| XXXIXa* | 9 | H | C=O | OH | HCl |
| XXXIXb* | 9 | H | C=O | OH | HI |

*Optical isomers

The compounds of formula (I) may be used in the treatment of hypertension in mammals, including humans, when administered in therapeutically effective amounts.

According to a further aspect of the present invention, therefore, there is provided a method for the treatment of hypertension in a mammal which comprises administering to said mammal a therapeutically effective amount of a compound of formula (I) or a pharmaceutically acceptable salt thereof.

According to further aspects, the invention also provides a compound of formula (I), or a pharmaceutically acceptable salt thereof, for use in therapy, for example, the treatment of hypertension, and for the use of a compound of formula (I), or a pharmaceutically acceptable salt thereof, in the manufacture of a therapeutic agent for the prophylaxis or treatment of hypertension.

The effective antihypertensive amount of active compound required for use in the above conditions will vary both with the route of administration, the condition under treatment and the mammal undergoing treatment, and is ultimately at the discretion of the physician. A suitable oral dose of the active compound for a mammal is in the range of from about 1 to about 50 mg per kilogram body weight per day; preferably from about 2 to about 20 mg/kg. For example, a typical dose for a human recipient of Compound (XVIII) is about 10 mg/kg body weight per day. The desired dose is preferably presented as from one to three sub-doses administered at appropriate intervals throughout the day. Where three sub-doses of compounds of formula (I) are employed, each will preferably lie in the range of from about 2 to about 7 mg/kg body weight; for example, a typical sub-dose of Compound (XVIII) for a human recipient is about 250 mg.

A suitable parenteral dose of the active compound for a mammal is in the range of from about 0.05 to about 5.0 mg per kilogram body weight per day, preferably from about 0.1 to about 4.0 mg/kg.

While it is possible for the active compound to be administered alone as the raw chemical, it is preferable to present the active compound as a pharmaceutical formulation. Formulations of the present invention, both for veterinary and for human medical use, comprise the active compound together with one or more pharmaceutically acceptable carriers therefor and optionally any other therapeutic ingredients. The carrier(s) must be pharmaceutically acceptable in the sense of being compatible with the other ingredients of the formulation and not deleterious to the recipient.

The formulations include those suitable for oral, transdermal, rectal or parenteral (including subcutaneous, intramuscular and intravenous) administration. Formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier, or both, and then, if necessary, shaping the product into the desired formulation.

Formulations of the present invention suitable for oral administration may be presented as discrete units such as capsules, cachets, tablets or lozenges, each containing a predetermined amount of the active compound; as a powder or granules; or as a suspension in an aqueous liquid or non-aqueous liquid such as a syrup, an elixir, an emulsion or a draught.

A tablet may be made by compression or molding, optionally with one or more accessory ingredients. Compressed tablets may be prepared by compressing in a suitable machine, the active compound being in a free-flowing form such as a powder or granules, optionally mixed with a binder, disintegrants, lubricant, inert diluent, or surface active/dispersing agent. Molded tablets, comprising a mixture of the powdered active compound with any suitable carrier, may be made by molding in a suitable machine. The tablets may optionally be coated or scored and may be formulated so as to provide slow or controlled release of the active ingredient therein. The tablets may optionally be provided with an enteric coating to release in parts of the gut other than the stomach.

A syrup may be made by adding the active compound to a concentrated, aqueous solution of a sugar; for example, sucrose, to which may also be added any accessory ingredient(s). Such accessory ingredient(s) may include flavorings, an agent to retard crystallization of the sugar or an agent to increase the solubility of any other ingredient, such as a polyhydric alcohol, for example, glycerol or sorbitol, and suitable preservatives.

Formulations suitable for parenteral administration conveniently comprise a sterile aqueous preparation of the active compound which is preferably isotonic with the blood of the recipient.

In addition to the aforementioned ingredients, the formulations of this invention may further include one or more accessory ingredient(s) selected from diluents, buffers, flavoring agents, binders, disintegrants, surface active agents, thickeners, lubricants, preservatives (including antioxidants) and the like.

When used in medicine, the salts of the compound of formula (I) should be pharmaceutically acceptable acid addition salts, but pharmaceutically unacceptable salts may conveniently be used to prepare the base or pharmaceutically acceptable salts of the base, and are not excluded from the scope of this invention. Suitable pharmaceutically acceptable salts include, but are not limited to, those prepared from the following acids: hydrochloric, hydrobromic, sulfuric, nitric, phosphoric, maleic, salicylic, toluene-p-sulfonic, tartaric, citric, acetic, methanesulfonic, formic, succinic, naphthalene-2-sulfonic, isethionic, lactobionic and benzenesulfonic.

EXAMPLES

The following Examples are provided by way of illustration of the present invention and should in no way be construed as a limitation thereof. All temperatures indicated are in degrees Celsius.

EXAMPLE 1

Preparation of stereoisomers of 4'-[1-Hydroxy-2-(((1,2,3,4-tetrahydro-1-oxo-2-naphthyl)methyl)amino)ethyl]methanesulfonanilide (XVIIIa and XVIIIb)

(a) Common reaction:

Compound (XXX) (12.9 g) and Compound (XXV).HCl (10.0 g) and triethylamine (7.4 ml) were combined in acetonitrile (150 ml) and stirred at ambient temperature. Within two hours the initial suspension became a clear solution, followed shortly thereafter by spontaneous precipitation of a white product. After stirring for 18 hours, the precipitate was filtered off and washed with acetonitrile, yielding 8.2 g of crude product.

(b) First Alternate Purification; Compound XVIIIa.

The 8.2 g of crude product from the reaction was dissolved by heating in 150 ml 90% EtOH containing concentrated HCl (4 ml), from which solution Compound (XVIIIa) precipitated as the HCl salt (6.5 g), m.p. 193°–196° (dec.). The analyses for C, H, and N were within 0.1% of predicted values. NMR and mass spectra were consistent with the structure indicated. HPLC analysis indicated that this compound was a mixture of the two expected diastereoisomers in similar amounts, variable from batch to batch.

(c) Second Alternate Purification; Compound XVIIIb.

4.6 g of crude product from a reaction similar to that above was suspended (not dissolved) in 38 ml of 95% EtOH at ambient temperature, and concentrated HCl (1.9 ml) was slowly added dropwise. After stirring 4 hours, the suspension was filtered and the solid was rinsed with EtOH (6 ml) and vacuum-dried, yielding Compound XVIIIb.HCl (4.5 g), m.p. 193°–195° (dec.). The elemental analysis for C, H, and N, NMR and mass spectra were consistent with the indicated structure and essentially the same as those of Compound XVIIIa.HCl above. However, the HPLC analysis of Compound XVIIIb.HCl indicated that the diastereoisomer ratio was 95:5 in favor of the component eluting later from a C-8 reverse phase column with a H₂O/acetonitrile mobile phase. By comparison with the HPLC retention of Compound XXXVIII (Example 8, below), it was determined that the predominant diastereoisomer in Compound XVIIIb was the R,S/S,R enantiomer pair.

A. Preparation of N-(1,2,3,4-Tetrahydro-1-oxo-2-naphthyl)methyl-N,N,N-trimethylammonium iodide (XXX)

Paraformaldehyde (43 g), 1-oxo-1,2,3,4-tetrahydronaphthalene (Aldrich Chemical Co., Milwaukee, Wis. 53233) (100 g), dimethylamine hydrochloride (61.5 g) and concentrated HCl (11.4 ml) were combined in EtOH (380 ml) and heated at reflux for 18 hours. Upon dilution with acetone (3000 ml) and cooling to 4°, a precipitate appeared, which was filtered off and partitioned between EtOAc and excess aqueous NaHCO₃. The EtOAc layer was dried (MgSO₄) and evaporated, leaving 79 g of oil. This oil was combined with methyl iodide (54 g) in acetone (100 ml) and stirred at ambient temperature for 1 hour. This resulted in precipitation of Compound (XXX) (96 g) as a white solid, m.p. 199°–200°, which was used without further purification.

B. Preparation of 4'-(2-Amino-1-hydroxyethyl)methanesulfonanilide (XXV)

4'-(2-Dibenzylaminoacetyl)methanesulfonanilide (XXVI) (32.7 g) and Pd/C catalyst (1.5 g) were combined in MeOH (200 ml), H₂O (25 ml), and concentrated HCl (6.6 ml) and shaken for 24 hours at 35° C. and 3 atmospheres pressure of hydrogen gas in a Parr hydrogenator, by which time three equivalents of hydrogen had been consumed. The catalyst was filtered off and the filtrate was evaporated to a white solid, which was recrystallized twice from 2-PrOH/H₂O. This yielded 4.3 g of Compound (XXV).HCl, m.p. 178°–180°, whose elemental analysis for C, H, and N, NMR, and mass spectra were consistent with the indicated structure.

C. Preparation of 4'-(2-Dibenzylaminoacetyl)methanesulfonanilide (XXVI)

4'-(2-Bromoacetyl)methanesulfonanilide (Temple, D. L. et al., J. Med. Chem., 19(5), 626–633 (1976)) (40 g) and dibenzylamine (Aldrich Chemical Co., Milwaukee, Wis. 53233) (55.2 g) were combined in acetone (550 ml) and stirred 3 hours at ambient temperature. A heavy precipitate of dibenzylamine.HBr was filtered off. The filtrate was evaporated and crystallized first from MeOH and then from 2-PrOH. This yielded the product, 4'-(2-dibenzylaminoacetyl)methanesulfonanilide (XXVI) as a crystalline solid, 42.9 g, m.p. 131°–134°, whose thin layer chromatography analysis (silica, EtOAc/hexane) and NMR indicated a single compound with the structure indicated above.

EXAMPLE 2

Preparation of 4'-[1-Hydroxy-2-(((1,2,3,4-tetrahydro-6-methoxy-1-oxo-2-naphthyl)methyl)amino)ethyl]methanesulfonanilide (XIX)

Compound (XXVII) (4.0 g), Compound (XXV).HCl (2.84 g), and triethylamine (1.5 ml) were combined in acetonitrile (40 ml) and stirred at ambient temperature for 18 hours. The acetonitrile was partially (about half) evaporated from the suspension, and the residue was triturated with EtOH (50 ml) and filtered. The resulting solid was crystallized twice, first from EtOH (50 ml) plus concentrated HCl (2 ml), and then from 90% EtOH, yielding Compound (XIX).HCl (2.6 g), m.p. 190°–194°, as a white solid. The analyses for C, H, and N were within 0.1% of predicted values. NMR and mass spectra were consistent with the structure indicated.

A. Preparation of N-(1,2,3,4-Tetrahydro-6-methoxy-1-oxo-2-naphthyl)-methyl-N,N,N-trimethylammonium iodide (XXVII)

Paraformaldehyde (24 g), 1-oxo-1,2,3,4-tetrahydro-6-methoxynaphthalene (Aldrich Chemical Co., Milwaukee, Wis. 53233) (40 g), dimethylamine hydrochloride (17.1 g) and concentrated HCl (4.5 ml) were combined in EtOH (150 ml) and heated at reflux for 18 hours. Dilution with acetone (1500 ml) and cooling to 4° produced white crystals of the intermediate Mannich base HCl salt (24 g). This was collected by filtration and partitioned between EtOAc and excess aqueous NaHCO$_3$. The EtOAc layer was washed with saturated NaCl solution, dried (MgSO$_4$) and evaporated to give 18 g of the oily free base. This oil was dissolved in acetone (200 ml), the solution was filtered, and methyl iodide (13.2 g) was added. The solution was heated at reflux for 15 minutes, cooled to 0°, and the resulting suspension was filtered, yielding Compound (XXVII) (28 g), as a white solid, m.p. 176°–177°, which was used without purification.

EXAMPLE 3

Preparation of
4'-[2-(((1,2,3,4-Tetrahydro-6-methoxy-1-oxo-2-naphthyl)methyl)amino)ethyl]methanesulfonanilide (XX)

Compound (XXVII) (8.1 g), Compound (XXVIII).HCl (5.5 g), and triethylamine (37.5 ml) were combined in acetonitrile (150 ml) and stirred at ambient temperature for 18 hours. The solvent was evaporated and the residue was purified by column chromatography on silica, eluting with CH$_2$Cl$_2$/MeOH (20:1 v/v). The product, Compound (XX), was heated with EtOH/concentrated HCl and evaporated to a solid, which was recrystallized from 90% EtOH, yielding Compound (XX).HCl as a white solid, 3.16 g, m.p. 208°–210° (dec.), whose NMR, mass spectra, and elemental analysis for C, H, and N were consistent with the structure indicated.

A. Preparation of 4'-(2-Aminoethyl)methanesulfonanilide (XXVIII)

4'-(2-Benzylaminoethyl)methanesulfonanilide (XXIX.HCl) (8.0 g) and 20% Pd/C (0.5 g) were combined in MeOH (200 ml) and heated at 40° for 18 hours in a Parr hydrogenator under an average hydrogen pressure of 3 atmospheres. The catalyst was filtered off. Concentration of the filtrate caused precipitation of Compound (XXVIII).HCl, 5.5 g as a white solid, m.p. 244°–246° (decomp.), whose elemental analysis for C, H, and N, and NMR spectrum were consistent with the structure indicated.

B. Preparation of 4'-(2-Benzylaminoethyl)methanesulfonanilide (XXIX)

2-(4-Methanesulfonamidophenyl)ethylmethanesulfonate (XXXII) (20 g), benzylamine (7.0 g) and triethylamine (15 ml) were combined in dimethylformamide (75 ml) and heated 18 hours at 100°. The solvent was evaporated and the residue was dissolved in EtOAc, which was washed with saturated NaHCO$_3$, dried (MgSO$_4$) and evaporated to give a dark oil. This was chromatographed on a silica column, eluting 8.0 g of solid product with CHCl$_3$/MeOH/concentrated NH$_4$OH (15:1:0.1). This solid was treated with MeOH/concentrated HCl (10:1), causing precipitation of 4'-(2-benzylaminoethyl)methanesulfonanilide.HCl (XXIX.HCl), m.p. 244°–245°, whose NMR was consistent with the proposed structure.

C. Preparation of 2-(4-Methanesulfonamidophenyl)ethylmethanesulfonate (XXXII)

2-(4-Methanesulfonamidophenyl)ethylmethanesulfonate (XXXII) was prepared from 2-(4-aminophenyl)ethanol (Aldrich Chemical Co., Milwaukee, Wis. 53233) (40.4 g) which was dissolved in pyridine (250 ml). Methanesulfonyl chloride (46 g) was added dropwise at ambient temperature. The reaction mixture was stirred for 18 hours and then poured onto ice. This caused separation of a pink solid, which was 2-(4-methanesulfonamidophenyl)ethylmethanesulfonate (XXXII), m.p. 132°–136°. Its NMR was consistent with the structure indicated, and it was used without further purification.

EXAMPLE 4

Preparation of
4'-[2-(((1,2,3,4-Tetrahydro-1-oxo-2-naphthyl)methyl)amino)ethyl]methanesulfonanilide (XXI)

Compound (XXX) (4.3 g), Compound (XXVIII).HCl (3.1 g) and triethylamine (25 ml) were combined in dimethylformamide (80 ml) and stirred at ambient temperature overnight. The reaction mixture was concentrated, and the residue was dissolved in 2N HCl, which was washed with ether, basified with concentrated NH$_4$OH, and extracted with EtOAc. The EtOAc was dried (MgSO$_4$) and evaporated. The residue was dissolved in MeOH/concentrated HCl and concentrated to form a solid. This was recrystallized from MeOH/EtOAc to yield Compound XXI.HCl (0.7 g), m.p. 209°–211°, which gave the correct elemental analysis for a ¼ hydrate. The NMR and mass spectral analyses were consistent with the structure indicated.

EXAMPLE 5

Preparation of
4'-[2-(((1,2,3,4-Tetrahydro-1-hydroxy-2-naphthyl)methyl)amino)ethyl]methanesulfonanilide (XXII)

Compound (XXI) (0.75 g) was combined with NaBH$_4$ (0.14 g) in MeOH (30 ml) and stirred at ambient temperature for 3½ hours. A further 0.14 g NaBH$_4$ was added and the reaction was stirred a further ½ hour. Acetone (10 ml) was added. After stirring 18 hours, the solvent was evaporated and the residue was partitioned between EtOAc and aqueous NaHCO$_3$. The EtOAc was evaporated, and the residue was chromatographed on a silica column, eluting the product with CH$_2$Cl$_2$/MeOH as a gummy solid (0.5 g). This was converted to its HCl salt using EtOH/concentrated HCl and recrystallized from EtOH to yield Compound XXII.HCl (0.2 g), m.p. 214°–220° (dec.). The elemental analysis for C, H, and N and mass spectra were consistent with the structure indicated. The NMR spectrum suggested that the 1,2-trans-isomer was the principal constituent, though some of the 1,2-cis-isomer was present also.

EXAMPLE 6

Preparation of
4'-[2-(((1,2,3,4-Tetrahydro-2-naphthyl)methyl)amino)ethyl]methanesulfonanilide (XXIII)

2-Aminomethyl-1,2,3,4-tetrahydronaphthalene (XXXI) (10 g) was dissolved in dimethylformamide (75 ml) containing triethylamine (25 ml) and heated to 100°. To this was added, in small portions over 3 hours, 2-(4-methanesulfonamidophenyl)ethylmethanesulfonate (XXXII) (19 g). After heating for a further 18 hours, the solvent was evaporated and the residue was taken up in EtOAc and washed with saturated NaHCO$_3$. The EtOAc was dried (MgSO$_4$) and evaporated, and the residue was chromatographed on a silica column, eluting the product with EtOAc/MeOH (20:1). The free amine was converted to its HCl salt by dissolving in MeOH, adding a small excess of concentrated HCl, adding EtOAc to the point of precipitation, and then concentrating the suspension by boiling. The product precipitated as a white solid, 4'-[2-(((1,2,3,4-tetrahydro-2-naphthyl)methyl)amino)ethyl]methanesulfonanilide.HCl (XXIII.HCl) m.p. 251°-253°, whose elemental analysis for C, H, and N, NMR and mass spectra were consistent with the proposed structure.

A. Preparation of 2-Aminomethyl-1,2,3,4-tetrahydronaphthalene (XXXI)

2-Nitromethyl-3,4-dihydronaphthalene (XXXV) (25 g) and 20% Pd/C (1.0 g) were combined in MeOH (200 ml) and shaken in a Parr hydrogenator at 3 atmospheres hydrogen pressure for 24 hours, by which time the theoretical amount of hydrogen (4 equivalents) had been absorbed. Removal of the catalyst and solvent left an oil (24 g) which was converted to its HCl salt by solution in MeOH and addition of concentrated HCl. The product, compound XXXI.HCl, was recrystallized from 2-propanol, yielding a white solid, m.p. 230° (dec.). Its elemental analysis and NMR spectrum were consistent with the structure indicated.

B. Preparation of 2-Nitromethyl-3,4-dihydronaphthalene (XXXV)

A solution of β-tetralone (Aldrich Chemical Co., Milwaukee, Wis. 53233) (24.5 gm) and ethylenediamine (1.75 gm) in nitromethane (250 ml) was heated at 80° for 16 hours. The reaction mixture was filtered, and the filtrate was evaporated to give a red oil. This was partially purified by elution through a short silica column, eluting with hexane/EtOAc (9:1 v/v). The product was a pink oil (26 gm) which was not purified further but was taken directly for the next reaction.

EXAMPLE 7

Preparation of 4'-[1-Hydroxy-2-(((1,2,3,4-tetrahydro-2-naphthyl)methyl)amino)ethyl]methanesulfonanilide (XXIV)

A mixture of 4'-[1-oxo-2-(N-benzyl-N-((1,2,3,4-tetrahydro-2-naphthyl)-methyl)amino)ethyl]methanesulfonanilide.HCl (XXXIII) (10 g) and 20% Pd/C (0.8 g) in MeOH (200 ml) was shaken 18 hours on a Parr hydrogenator at an average pressure of 3 atmospheres, during which time two equivalents of hydrogen were absorbed. The reaction mixture was filtered and the solvent was evaporated to give a solid, which was recrystallized from MeOH. The product, 4'-[1-hydroxy-2-(((1,2,3,4-tetrahydro-2-naphthyl)methyl)amino)-ethyl]-methanesulfonanilide.HCl (XXIV.HCl), was collected as two separate crops. The first crop, 3.5 g, had a m.p. of 204°-206°. The second crop, 1.5 g, obtained from the mother liquor by adding EtOAc and concentrating by boiling, had a m.p. of 223°-225°. Both crops had elemental analyses and mass spectra consistent with the structure indicated. Carbon-13 NMR indicated that the two crops of product differed in the relative amounts of the diastereoisomers present.

A. Preparation of 4'-[1-Oxo-2-(N-benzyl-N-((1,2,3,4-tetrahydro-2-naphthyl)-methyl)amino)ethyl]methanesulfonanilide (XXXIII)

2-Benzylaminomethyl-1,2,3,4-tetrahydronaphthalene (XXXIV) (2.8 g), N,N-diisopropyl-N-ethylamine (1.44 g) and 4'-(2-bromoacetyl)methanesulfonanilide (Temple, D. L. et al., J. Med. Chem., 19(5), 626–633 (1976)) (3.27 g) were dissolved in acetone (40 ml) and stirred 18 hours at ambient temperature. The solvent was evaporated and the residue was dissolved in $CH_2Cl_2$, which was washed with $H_2O$, dried ($MgSO_4$) and evaporated. The HCl salt was made by dissolving the residue in MeOH/concentrated HCl, concentrating, and triturating the residue with 2-PrOH and ether. The solid product, 4'-[1-oxo-2-(N-benzyl-N-((1,2,3,4-tetrahydro-2-naphthyl)methyl)-amino)ethyl]methanesulfonanilide.HCl (XXXIII.HCl), 3 g, had NMR and mass spectra consistent with the structure indicated. It was used without further purification.

B. Preparation of 2-Benzylaminomethyl-1,2,3,4-tetrahydronaphthalene (XXXIV)

A solution of 2-aminomethyl-1,2,3,4-tetrahydronaphthalene (XXXI) (14.5 g), benzaldehyde (9.7 g) and $NaBH_3CN$ (5.8 g) in methanol (150 ml) was cooled to 0°. Concentrated HCl was added dropwise until the apparent pH (litmus) was 3–4. The mixture was then stirred 16 hours at 0°. The solvent was evaporated, and the residue was dissolved in EtOAc, which was washed with saturated $NaHCO_3$ solution, dried ($MgSO_4$), and evaporated. The residual oil was dissolved in MeOH, and a slight excess of concentrated HCl was added. Adding EtOAc and boiling caused precipitation of Compound XXXIV.HCl, which was collected by filtration. Its NMR was consistent with the structure indicated, and it was used without further purification.

EXAMPLE 8

Preparation of 4'-[1-(S)-Hydroxy-2-(((1,2,3,4-tetrahydro-1-oxo-2-(R,S)-naphthyl)methyl)amino)ethyl]methanesulfonanilide (XXXVII) and its stereoisomers 4'-[1-(S)-hydroxy-2-(((1,2,3,4-tetrahydro-1-oxo-2-(S)-naphthyl)methyl)amino)ethyl]methanesulfonanilide (XXXVIIIa) and 4'-[-1-(S)-hydroxy-2-(((1,2,3,4-tetrahydro-1-oxo-2-(R)-naphthyl)methyl)amino)ethyl]methanesulfonanilide (XXXVIIIb)

Compound XXX (3.9 g) and Compound S-(+)-XXV.HCl (3.0 g) and triethylamine (2.1 ml) were combined in acetonitrile (50 ml), and the suspension was stirred at ambient temperature. The solid slowly passed into solution, followed within 2 hours by precipitation of a white solid product. The suspension was then stirred 2 hours at 0° and filtered, yielding a filtrate (saved for subsequent treatment) and 2.0 g of a white solid, m.p. 114°-117°, $\alpha^{20}D = +35.9°$ (c=1, MeOH). The elemental analysis (3.1% I–, trace Cl–) of this solid indicated that it was predominantly the free base of the desired product, along with small amounts of addition salts. Of this material, 1.9 g was converted to the HCl salt by suspending in 5.5 ml concentrated HCl and 14.5 ml distilled $H_2O$, stirring at 0° for 2 hours, filtering of the resulting solid, and finally recrystallizing from 95% EtOH. This yielded 1.1 g of XXXVII.HCl, m.p. 168°-170° (dec., after apparently losing $H_2O$ at 104°), $\alpha^{20}D = +29.9°$ (c=1, MeOH), whose NMR and mass spectra were consistent with the structure indicated and whose elemental analyses for C, H, and N were within 0.1% of values predicted for the hemihydrate. HPLC analysis of this compound indicated that it was a mixture of the two possible diastereoisomers in similar amounts whose ratio was variable from batch to batch, with consequent slightly variable effects on physical properties (m.p., $\alpha^{20}$D).

One of the individual diastereoisomers was obtained from the filtrate from the original reaction above. That acetonitrile solution was evaporated to a volume of 10 ml and cooled to $-15°$ for 18 hours, resulting in precipitation of a solid which was recrystallized three times from 95% EtOH. This yielded 0.4 g of Compound XXXVIIIa.HI, m.p. 204°-207° (dec.), $\alpha^{20}$D = +73.7° (c=0.4, MeOH) whose elemental analyses for C, H, and N, NMR and mass spectra were consistent with the structure indicated. HPLC analysis indicated that a single diastereoisomer was present, and X-ray analysis showed that it had the S,S absolute configuration.

The other stereoisomer was obtained by preparative HPLC. In each of five separate runs, 0.050 g of XXXVII.HCl dissolved in 5 ml of starting solvent mixture (87% A + 13% B; solvent A = H₂O + 1% triethylamine + 2% formic acid; solvent B = acetonitrile) was passed through a HPLC column (Supelcosil® PLC-8, 25 cm × 21.2 mm, 18 μm particle size) using a flow rate of 70 ml/min and a solvent gradient of 87% A to 83% A in 30 min. This resulted in partial separation of the diastereoisomers. Fractions (20-100 ml each) were acidified immediately by addition of concentrated HCl and then analyzed by analytical HPLC. Fractions containing ≧75% of the longer-retained isomer XXXVIIIb were pooled and evaporated at 35° C. to a volumne of 150 ml. This solution was then brought to pH 7 (litmus) with NaHCO₃, extracted with CH₂Cl₂ and the extract was dried (MgSO₄) and evaporated to a glassy residue. This residue was stirred with 6 ml of 1N HCl plus 6 ml saturated NaCl solution, resulting in a suspension of white solid which was filtered to yield partially purified XXXVIIIb.HCl. It was repurified by repeating the preparative HPLC just described, this time combinining only fractions containing >95% of the single diastereoisomer XXXVIIIb. When these fractions were combined and treated as described above, the resulting total solid (25 mg) consisted of 83% XXXVIIIb.HCl and 17% XXXVIIIa.HCl (by analytical HPLC), m.p. 100°-103° (dec.), whose NMR and mass spectra were consistent with the indicated structure and whose optical rotations (c=0.4, MeOH, 20° C.) were: λ=589, α=0.0°; λ=436, α=−9.7°; λ=365, α=−108°.

A. Preparation of
S-(+)-4'-(2-Amino-1-hydroxyethyl)methanesulfonanilide (S-(+)-XXV)

(+)-4'-(2-Dibenzylamino-1-hydroxyethyl)methanesulfonanilide (S-(+)-XXXVI), $\alpha^{20}$D = +33.8° (c=2, MeOH), (14.5 g); 20% Pd/C catalyst (1.5 g) and concentrated HCl (3.0 ml) were combined in EtOH (200 ml) and shaken for 20 hours at 35° at 3 atmospheres pressure of hydrogen gas in a Parr hydrogenator, by which time two equivalents of hydrogen had been consumed. The catalyst was filtered and the filtrate was evaporated from MeOH/EtOAc. This yielded 6.6 g of Compound (S-(+)-XXV).HCl, m.p. 190°-191.5° (dec.), $\alpha^{20}$D = +45.8° (c=2, MeOH), whose elemental analysis for C, H, and N, NMR and mass spectra were consistent with the indicated structure. The absolute configuration was determined to be S by X-ray analysis of a correlatable compound, XXXVIII.

B. Preparation of
R-(−)-4'-(2-Amino-1-hydroxyethyl)methanesulfonanilide (R-(−)-XXV)

This compound was prepared by the method shown above for its enantiomer, (S-(+)-XXV). Thus, hydrogenolysis of (R-(−)-XXXVI), $\alpha^{20}$D = −33.8° (c=2, MeOH), (12.0 g) yielded 4.7 g of (R-(−)-XXV).HCl, m.p. 187.5°-189° (dec.), $\alpha^{20}$D = −46.9° (c=2, MeOH), whose elemental analysis for C, H, and N, NMR and mass spectra were consistent with the indicated structure. The absolute configuration was determined to be R by X-ray analysis of a correlatable compound, XXXVIII.

C. Preparation of
S-(+)-4'-(2-Dibenzylamino-1-hydroxyethyl)methanesulfonanilide (S-(+)-XXXVI)

(+)-B-Chlorodiisopinocampheylborane (Aldrich Chemical Co., Milwaukee, WI 53233) (16.5 g) and Compound XXVI (20.0 g) were combined in dry tetrahydrofuran under N₂ at −25°. The mixture was stirred at −25° for 7 hours and then allowed to stand at 0° for 18 hours. The solvent was evaporated and replaced by a mixture of ether (400 ml) and diethanolamine (11.6 g). The mixture was then stirred at 25° for 3 hours, filtered, and the filtrate was evaporated to dryness. The residue was combined with the corresponding material from an identical preparation and chromatographed on a silica gel column. Product was eluted with EtOAc/hexane (1:3). The product was crystallized from 2-PrOH, yielding (S-(+)-XXXVI), 14.9 g, m.p. 80°-98° $\alpha^{20}$D = +33.8° (c=2, MeOH), whose NMR was consistent with the indicated structure. It was taken for hydrogenolysis without further purification. The absolute stereochemistry was determined to be S by X-ray analysis of a correlatable compound, XXXVIII.

D. Preparation of
R-(−)-4'-(2-Dibenzylamino-1-hydroxyethyl)methanesulfonanilide (R-(−)-XXXVI)

This compound was prepared by the method shown above for its enantiomer, (S-(+)-XXXVI). Thus, when Compound XXVI (39.0 g) was reduced analogously with (−)-B-chlorodiisopinocampheylborane (Aldrich Chemical Co., Milwaukee, WI 53233) (32.2 g), the product after crystallization from 2-PrOH was Compound (R-(−)-XXXVI), 12.2 g, m.p. 82°-100°, $\alpha^{20}$D = −33.8° (c=2, MeOH), whose NMR was consistent with the structure indicated. It was taken for hydrogenolysis without further purification. The absolute configuration was determined to be R by X-ray analysis of a correlatable compound, XXXVIII.

EXAMPLE 9

Preparation of
4'-[1-(R)-Hydroxy-2-(((1,2,3,4-tetrahydro-1-oxo-2-(R,S)-naphthyl)methyl)amino)ethyl]methansulfonanilide (XXXIXa) and its stereoisomers
4'[1-(R)-hydroxy-2-(((1,2,3,4-tetrahydro-1-oxo-2-(R)-naphthyl)methyl)amino)ethyl]methanesulfonanilide (XXXIXb) and
4'-[1-(R)-hydroxy-2-(((1,2,3,4-tetrahydro-1-oxo-2-(S)-naphthyl)methyl)amino)ethyl]methanesulfonanilide (XXXIXc)

These compounds were prepared by a method similar to that shown above for their optical antipodes, XXXVII and XXXVIII. Thus, when Compound XXX (5.8 g) and Compound R-(−)-XXV.HCl (4.5 g) and triethylamine (3.1 ml) were reacted at ambient temperature in acetonitrile (75 ml), a solid and a filtrate were obtained. To convert all the solid to the HCl addition salt, it was suspended in concentrated HCl (7 ml) and H$_2$O (20 ml), stirred at 0° for 2 hours, and then filtered. Recrystallization from 2-PrOH/H$_2$O yielded 1.7 g of XXXIXa.HCl, m.p. 100.5°–104° (apparently losing H$_2$O), $\alpha^{20}_D = -29.6°$ (c=1, MeOH), whose NMR and mass spectra were consistent with the structure indicated and whose elemental analyses for C, H, and N were within 0.15% of values predicted for a monohydrate. HPLC analysis indicated that the compound had been obtained as a mixture of the two possible diastereoisomers in approximately equal amounts. The absolute configuration was inferred by X-ray analysis of a correlatable compound, XXXVIII.

One of the individual diastereoisomers was obtained from the original acetonitrile filtrate from a similar reaction run on 1.5× scale. The filtrate was evaporated to a volume of 25 ml and cooled to −15° for 18 hours, resulting in precipitation of a solid which was rinsed with EtOAc and recrystallized from aqueous EtOH. This yielded 1.8 g of Compound XXXIXb.HI, m.p. 200°–201° (dec.), $\alpha^{20}_D = -72.1°$ (c=0.42, MeOH) whose elemental analyses for C, H, and N, NMR and mass spectra were consistent with the structure indicated. HPLC analysis indicated that a single diastereoisomer (≥95%) was present having the R,R absolute configuration, by correlation with the structure of Compound XXXVIII (Example 8, above).

The other diastereoisomer was obtained by preparative HPLC by the method described in Example 8 for its enantiomer XXXVIIIb. The product consisted of 85% XXXIXc.HCl and 15% of XXXIXb.HCl (by analytical HPLC), m.p. 100°–103° (dec.), whose NMR and mass spectra were consistent with the indicated structure and whose optical rotations (c=0.4, MeOH, 20° C.) were: $\lambda$=589, $\alpha$=0.0°; $\lambda$=436, $\alpha$=+7.9°; $\lambda$=365, $\alpha$=+112°.

EXAMPLE 10

Antihypertensive Activity

The blood pressure lowering activities of compounds of formula (I) were evaluated in conscious, genetically hypertensive rats (Charles River Breeding Laboratories, Inc., Wilmington, Mass. 01887.) The results of these studies are summarized in Table I for a selected number of compounds.

Spontaneously Hypertensive Rats

Spontaneously hypertensive rats (Charles River), weighing between 300–450 g, were used in this study. Systolic and diastolic blood pressure measurements were made directly from the indwelling arterial cannula.

On the day of surgery, rats were anesthetized with sodium pentobarbital, 50 mg/kg, i.p. The right femoral artery was cannulated with a polyethylene tube (PE50, i.d. 0.023"), filled with 10% heparinized saline, the tip of which was drawn to approximately the size of a PE10 tube (i.d. 0.011"). The tip of the cannula was advanced into the aorta just below the level of the kidneys. The opposite end of the cannula was passed under the skin and exteriorized at the back of the neck near the shoulder blades. It was then passed through a metal spring tether and a saddle (BRS/LVE, Beltsville, Md) which was stitched and taped to the back of the rat. Rats were housed in individual cages and allowed to recover for three days. Patency of the cannula was maintained by withdrawing heparinized saline, flushing with normal saline and then replacing the cannula dead space with 10% heparinized saline (0.3 ml).

Blood pressure was continuously monitored using a Statham pressure transducer (p23id) and recorded on a Grass polygraph (Model 7) and the readings were digitized using a cardiovascular analyzer and a data logger (Buxco Electronics).

On experimental day one, control (baseline) blood pressure readings were obtained for 3 hours and were averaged. The test compound was administered p.o. or i.p. and the blood pressure monitored for the next 24 hours. This was followed by the next dose of the test compound and the procedure was repeated for the next 2–3 days. Blood pressure was continuously monitored and the readings were averaged for each hour after administering the test compound. Changes in systolic and diastolic blood pressures from control (pre-drug) values were expressed in percent.

Compounds were dissolved in distilled water (for oral dosing) or normal saline (for i.p. injection). 0.5% Methyl cellulose was used as the vehicle in some cases. The injection volume was 0.1–0.2 ml/100 g body weight.

TABLE I

Blood Pressure Lowering Activity of Selected Compounds in Spontaneously Hypertensive Rats

| Compound | Dose mg/kg p.o. | % Decrease in Blood Pressure (mmHg) Systolic/Diastolic |
|---|---|---|
| XVIIIa | 3 | 15 ± 1.5/18 ± 1.6 |
| | 10 | 21 ± 1.2/22 ± 1.5 |
| | 30 | 28 ± 1.7/30 ± 2.0 |
| XVIIIb | 3 | 19 ± 2.5/19 ± 2.5 |
| | 10 | 21 ± 2.2/23 ± 1.7 |
| | 30 | 30 ± 4.5/32 ± 5.6 |
| XIX | 3 | 16 ± 2/16 ± 3 |
| | 10 | 19 ± 2/21 ± 3 |
| | 30 | 26 ± 5/26 ± 6 |
| XX | 3 | 16 ± 2/15 ± 3 |
| | 10 | 20 ± 2/20 ± 2 |
| | 30 | 28 ± 2/31 ± 2 |
| XXI | 5 | 18 ± 4/23 ± 3 |
| | 10 | 30 ± 3/36 ± 4 |
| XXII | 3 | 13 ± 3/13 ± 3 |
| | 10 | 22 ± 2/26 ± 2 |
| | 30 | 31 ± 5/34 ± 6 |
| XXIII | 3 | 17 ± 2/18 ± 2 |
| | 10 | 24 ± 3/23 ± 2 |
| | 30 | 26 ± 3/31 ± 3 |
| XXIV | 3 | 14 ± 1/17 ± 2 |
| | 10 | 16 ± 1/18 ± 3 |
| | 30 | 25 ± 2/26 ± 2 |
| XXXVII | 3 | 18 ± 1.5/22 ± 2.7 |
| | 10 | 28 ± 2.4/31 ± 2.3 |
| | 30 | 33 ± 1.1/37 ± 1.3 |
| XXXVIIIa | 3 | 15 ± 1.5/17 ± 1.7 |
| | 10 | 24 ± 2.5/26 ± 3.0 |
| | 30 | 24 ± 2.1/30 ± 2.4 |
| XXXIXa | 3 | 7 ± 1/10 ± 2 |
| | 10 | 16 ± 1.9/19 ± 1.6 |
| | 30 | 24 ± 2/30 ± 2.5 |
| XXXIXb | 3 | 9 ± 2.5/9 ± 3.1 |
| | 10 | 15 ± 2.1/18 ± 3 |
| | 30 | 19 ± 1.9/25 ± 2.8 |

EXAMPLE 11

Formulations

| A-Injection | |
|---|---|
| Ingredient | Amount per ampule |
| Compound of Formula I | 250.0 mg |
| Sodium Chloride | 8.5 mg |
| Water for Injections, q.s. | 1.0 mL |

The finely ground active compound and sodium chloride are dissolved in the Water for Injections. The solution is filtered and sterilized by autoclaving.

| B-Suppository | |
|---|---|
| Ingredient | Amount per suppository |
| Compound of Formula I | 250.0 mg |
| Cocoa Butter, q.s. or Wecobee ™ Base | 2.0 g |

Wecobee is the trademark of a hydrogenated carboxylic acid.

The finely ground active compound is mixed with the melted suppository base (either Cocoa Butter or Wecobee ™ Base), poured into molds and allowed to cool to afford the desired suppositories.

| C-Syrup | |
|---|---|
| Ingredient | Amount per 5 mL |
| Compound of Formula I | 250.0 mg |
| Glycerol | 500.0 mg |
| Sucrose | 3500.0 mg |
| Methylparaben | 5.0 mg |
| Cherry Flavoring | 0.005 mL |
| Coloring | q.s. |
| Water | q.s. to 5.0 mL |

Glycerol, sucrose, methylparaben, and flavoring are combined in 70% of the total batch quantity of water. Coloring and the active compound are dissolved in the remaining water. Coloring and the active compound are dissolved in the remaining water, then the two solutions are mixed and clarified by filtration.

| D-Tablet | |
|---|---|
| Ingredient | Amount per Tablet |
| Compound of Formula I | 250.0 mg |
| Lactose | 125.0 |
| Corn Starch | 50.0 |
| Polyvinylpyrrolidone | 3.0 |
| Stearic acid | 1.0 |
| Magnesium stearate | 1.0 |

The active compound is finely ground and intimately mixed with the powdered excipients lactose, corn starch, polyvinylpyrrolidone, magnesium stearate and stearic acid. The formulation is then compressed to afford a tablet weighing 430 mg.

| E-Capsule | |
|---|---|
| Ingredient | Amount per Capsule |
| Compound of Formula I | 250.0 mg |
| Lactose | 174.0 |
| Corn Starch | 174.0 |
| Stearic Acid | 2.0 |

The finely ground active compound is mixed with the powdered excipients lactose, corn starch and stearic acid and packed into gelatin capsules.

EXAMPLE 12

Toxic Effects

For rats, $LD_{50} > 250$ mg/kg p.o. was determined. The $LD_{50}$ for mice was ~250 mg/kg i.p.

We claim:

1. A compound of formula (I)

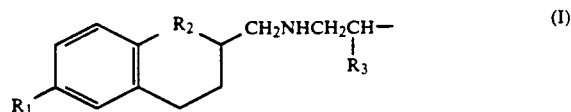

wherein
$R_1$ is hydrogen;
$R_2$ is carbonyl; and
$R_3$ is hydroxy;
or a salt thereof.

2. A compound of formula (I) as claimed in claim 1 which is
4'-[1-hydroxy-2-(((1,2,3,4-tetrahydro-1-oxo-2-naphthyl)methyl)amino)ethyl]methanesulfonanilide
in any of its enantiomeric, diastereomeric, or racemic forms or as a mixture of two or more such forms in any proportions; or a pharmaceutically acceptable salt thereof.

3. The hydrochloride or hydroiodide salt of a compound of formula (I) as claimed in claim 2.

4. A method for the treatment of hypertension in a mammal which comprises administering to said mammal a therapeutically effective antihypertensive amount of a compound of formula (I) or of a pharmaceutically acceptable salt thereof as claimed in claims 1, 2 or 3.

5. A pharmaceutical formulation comprising a compound of formula (I) or a pharmaceutically acceptable salt thereof as claimed in claims 1, 2 or 3, and one or more pharmaceutically acceptable carriers therefor.

6. A compound of formula (I) as claimed in claim 1 which is
4'-[1-(S)-Hydroxy-2-(((1,2,3,4-tetrahydro-1-oxo-2-(R,S)-naphthyl)methyl)amino)ethyl]methanesulfonanilide
or a pharmaceutically acceptable salt thereof.

7. A compound of formula (I) as claimed in claim 1 which is
4'-[1-(S)-hydroxy-2-(((1,2,3,4-tetrahydro-1-oxo-2-(S)-naphthyl)methyl)amino)ethyl]methanesulfonanilide
or a pharmaceutically acceptable salt thereof.

8. A compound of formula (I) as claimed in claim 1 which is
4'-[-1-(S)-hydroxy-2-(((1,2,3,4-tetrahydro-1-oxo-2-(R)-naphthyl)methyl)amino)ethyl]methanesulfonanilide
or a pharmaceutically acceptable salt thereof.

9. A compound of formula (I) as claimed in claim 1 which is

4'-[1-(R)-Hydroxy-2-(((1,2,3,4-tetrahydro-1-oxo-2-(R,S)-naphthyl)methyl)amino)ethyl]methanesulfonanilide or a pharmaceutically acceptable salt thereof.

10. A compound of formula (I) as claimed in claim 1 which is

4'-[1-(R)-hydroxy-2-(((1,2,3,4-tetrahydro-1-oxo-2-(R)-naphthyl)methyl)amino)ethyl]methanesulfonanilide or a pharmaceutically acceptable salt thereof.

11. A compound of formula (I) as claimed in claim 1 which is

4'-[1-(R)-hydroxy-2-(((1,2,3,4-tetrahydro-1-oxo-2-(S)-naphthyl)methyl)amino)ethyl]methanesulfonanilide or a pharmaceutically acceptable salt thereof.

12. The compound 4'-[1-hydroxy-2-(((1,2,3,4-tetrahydro-1-oxo-2-naphthyl)methyl)amino)ethyl]methanesulfonanilide.

13. A pharmaceutical formulation of the compound of claim 12 and one or more pharmaceutically acceptable carriers therefor.

14. A method for the treatment of hypertension in a mammal which comprises administering to said mammal a therapeutically effective antihypertensive amount of the compound of claim 12.

15. A pharmaceutically acceptable salt of 4'-[1-hydroxy-2-(((1,2,3,4-tetrahydro-1-oxo-2-naphthyl)methyl)amino)ethyl]methanesulfonanilide.

16. A pharmaceutical formulation of the compound of claim 15 and one or more pharmaceutically acceptable carriers therefor.

17. A method for the treatment of hypertension in a mammal which comprises administering to said mammal a therapeutically effective antihypertensive amount of the compound of claim 15.

18. The hydrochloride salt of the compound of claim 15.

19. A method of treating a mammal having hypertension, which comprises orally or paraenerally administering to said mammal an effective hypertension treatment amount of a pharmaceutically acceptable acid addition salt of 4'-[1-hydroxy-2-(((1,2,3,4-tetrahydro-1-oxo-2-naphthyl)methyl)amino)ethyl]methanesulfonanilide.

20. The method of claim 19, in which the salt administered is the hydrochloride, hydroiodide, sulfuric or methanesulphonic salt.

21. The method of claim 19, in which the sulfuric or methanesulphonic salt is administered.

22. A method of treating a mammal having hypertension, which comprises orally or paraenerally administering to said mammal an effective hypertension treatment amount of a pharmaceutically acceptable acid addition salt of 4'-[1-(S)-hydroxy-2-(((1,2,3,4-tetrahydro-1-oxo-2-(R,S)-naphthyl)methyl)amino)ethyl]methanesulfonanilide.

23. The method of claim 22, in which the salt administered is the hydrochloride, hydroiodide, sulfuric or methanesulphonic salt.

24. The method of claim 22, in which the sulfuric or methanesulphonic salt is administered.

25. A method of treating a mammal having hypertension, which comprises orally or paraenerally administering to said mammal an effective hypertension treatment amount of a pharmaceutically acceptable acid addition salt of 4'-[1-(S)-hydroxy-2-(((1,2,3,4-tetrahydro-1-oxo-2-(S)-naphthyl)methyl)amino)ethyl]methanesulfonanilide.

26. The method of claim 25, in which the salt administered is the hydrochloride, hydroiodide, sulfuric or methanesulphonic salt.

27. The method of claim 25, in which the sulfuric or methanesulphonic salt is administered.

28. A tablet or capsule containing an effective hypertension treatment amount of a pharmaceutically acceptable acid addition salt of 4'-[1-hydroxy-2-(((1,2,3,4-tetrahydro-1-oxo-2-naphthyl)methyl)amino)ethyl]methanesulfonanilide and a pharmaceutically acceptable carrier therefore.

29. The tablet or capsule of claim 28, in which the salt is the hydrochloride, hydroiodide, sulfuric or methanesulfulphonic salt.

30. A tablet or capsule containing an effective hypertension treatment amount of a pharmaceutically acceptable acid addition salt of 4'-[1-(S)-hydroxy-2-(((1,2,3,4-tetrahydro-1-oxo-2-(R,S)-naphthyl)methyl)amino)ethyl]methanesulfonanilide and a pharmaceutically acceptable carrier therefore.

31. The tablet or capsule according to claim 30, in which the salt is the hydrochloride, hydroioide, sulfuric or methanesulfulphonic salt.

32. A tablet or capsule containing an effective hypertension treatment amount of a pharmaceutically acceptable acid addition salt of 4'-[1-(S)-hydroxy-2-(((1,2,3,4-tetrahydro-1-oxo-2-(S)-naphthyl)methyl)amino)ethyl]methanesulfonanilide.

33. The tablet or capsule, in which the salt is the hydrochloride, hydroiodide, sulfuric or methanesulfulphonic salt.

34. A pharmaceutically acceptable acid addition salt of 4'-[1-hydroxy-2-(((1,2,3,4-tetrahydro-1-oxo-2-naphthyl)methyl)amino)ethyl]methanesulfonanilide.

35. A pharmaceutically acceptable acid addition salt of 4'-[1-(S)-hydroxy-2-(((1,2,3,4-tetrahydro-1-oxo-2-(R,S)-naphthyl)methyl)amino)ethyl]methanesulfonanilide.

36. A pharmaceutically acceptable acid addition salt of 4'-[1-(S)-hydroxy-2-(((1,2,3,4-tetrahydro-1-oxo-2-(S)-naphthyl)methyl)amino)ethyl]methanesulfonanilide.

37. The salt of claim 34, which is derived from hydrochloric acid, hydroiodic acid, methane sulphonic acid or sulfuric acid.

38. The salt of claim 35, which is derived from hydrochloric acid, hydroiodic acid, methane sulphonic acid or sulfuric acid.

39. The salt of claim 36, which is derived from hydrochloric acid, hydroiodic acid, methane sulphonic acid or sulfuric acid.

* * * * *